(12) United States Patent
McCarthy

(10) Patent No.: US 8,636,723 B2
(45) Date of Patent: Jan. 28, 2014

(54) DRAINAGE APPARATUS AND SYSTEM

(76) Inventor: George McCarthy, Bowdon (GB)

( * ) Notice: Subject to any disclaimer, the term of this patent is extended or adjusted under 35 U.S.C. 154(b) by 425 days.

(21) Appl. No.: 12/595,617

(22) PCT Filed: Apr. 10, 2008

(86) PCT No.: PCT/GB2008/001241
§ 371 (c)(1),
(2), (4) Date: May 14, 2010

(87) PCT Pub. No.: WO2008/125812
PCT Pub. Date: Oct. 23, 2008

(65) Prior Publication Data
US 2010/0286666 A1  Nov. 11, 2010

(30) Foreign Application Priority Data

Apr. 17, 2007  (GB) .................................. 0707381.0
Nov. 10, 2007  (GB) .................................. 0722118.7

(51) Int. Cl.
*A61M 1/00*  (2006.01)

(52) U.S. Cl.
USPC ........................... 604/544; 604/540; 52/173.1

(58) Field of Classification Search
USPC .................. 604/317, 327, 540, 544; 52/173.1
See application file for complete search history.

(56) References Cited

U.S. PATENT DOCUMENTS

| | | | | | |
|---|---|---|---|---|---|
| 2,258,017 | A | * | 10/1941 | King | 285/364 |
| 3,749,096 | A | * | 7/1973 | Donaldson | 604/351 |
| 6,001,086 | A | * | 12/1999 | Rammacher | 604/327 |
| 2004/0176746 | A1 | * | 9/2004 | Forral | 604/544 |
| 2006/0096016 | A1 | | 5/2006 | Krowl | |
| 2006/0253090 | A1 | | 11/2006 | Bradley et al. | |
| 2007/0010798 | A1 | * | 1/2007 | Stoller et al. | 604/544 |

FOREIGN PATENT DOCUMENTS

| | | | | |
|---|---|---|---|---|
| BE | 1001716 A7 | 2/1990 | | |
| BE | A-1 001 7167 | 2/1990 | | |
| EP | 1 520 565 A2 | 9/2004 | | |
| EP | 1520565 A | 4/2005 | | |
| EP | 1520565 A2 * | 4/2005 | | |
| FR | 2590480 A | 5/1987 | | |
| FR | A-2 590 480 | 5/1987 | | |
| GB | 2061731 A * | 5/1981 | ............... | A61F 5/00 |
| JP | 49-003496 A | 1/1974 | | |
| JP | 2000-325258 A | 11/2000 | | |
| JP | 2001-025484 A | 1/2001 | | |
| WO | WO 2007018963 A2 * | 2/2007 | ............... | A61B 5/03 |
| WO | WO 2008/125812 A | 10/2008 | | |

OTHER PUBLICATIONS

International Search Report for International Application No. PCT/GB2008/001241 (Jul. 22, 2008).

(Continued)

*Primary Examiner* — Jacqueline Stephens
*Assistant Examiner* — Benedict L Hanrahan
(74) *Attorney, Agent, or Firm* — Jenkins, Wilson, Taylor & Hunt, P.A.

(57) ABSTRACT

A drainage apparatus for an incapacitated person or ostomy patient having a urine draining device or stoma respectively, the apparatus comprising a conduit (14) having a first end having connection means suitable to attach to the urine draining device or stoma of the person or patient and a second end connected to a sewer/drainage system (20) of a dwelling (8). Such dwellings may include commercial and domestic buildings, caravans and motor homes and a portion of the conduit may be permanent in such a dwelling.

6 Claims, 3 Drawing Sheets

(56) References Cited

OTHER PUBLICATIONS

Figure 1:
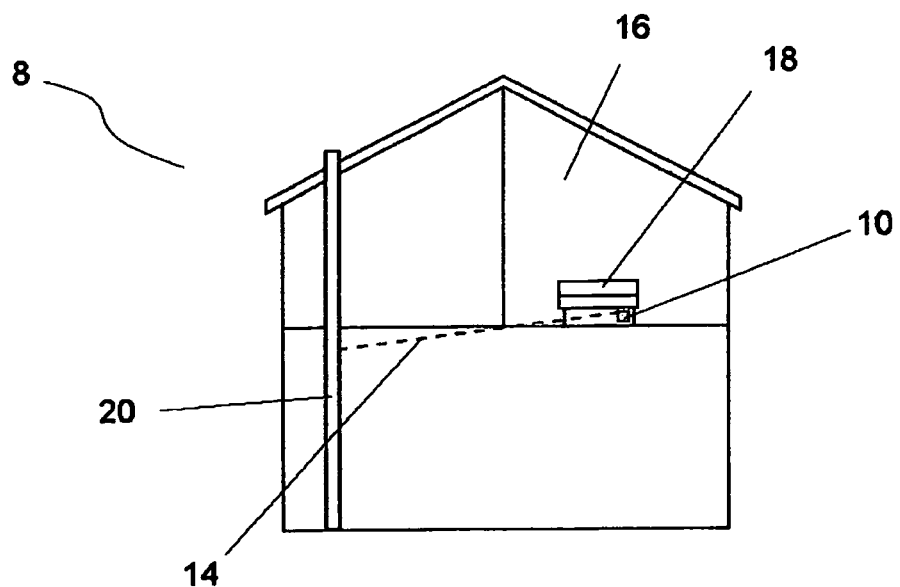

Abbreviated Examination Report under Section 18(3) for Application No. GB0722118.7 (Jul. 24, 2009).

Search Report under Section 17 for Application No. GB0722118.7 (Feb. 21, 2008).

Notification Concerning Transmittal of International Preliminary Report on Patentability for International Application No. PCT/GB2008/001241 (Oct. 20, 2009).

* cited by examiner

DRAINAGE APPARATUS AND SYSTEM

The present invention relates generally to a drainage apparatus and kit for people who have difficulties or disorders relating to dealing with waste material expelled from the body. The invention particularly relates to apparatus for people who are incapacitated or to patients who have undergone an ostomy operation. Ostomy patients include people who have undergone a colostomy or urostomy operation. The present invention specifically relates to a drainage apparatus and kit for disabled, urostomy or colostomy patients suitable for use during the night or other extended periods spent in bed or when otherwise immobile, such as when in hospital, in a wheelchair or when bed-bound.

For convenience, the term 'incapacitated' has been used to include people for whom it is difficult or impossible to void waste material, typically urine or faeces, through the normal urinary or defecation process, e.g. severely disabled people. Incapacitated people may also find it impossible or extremely difficult to reach a suitable convenience in time, even if they are capable of performing normal urination or defecation. Such people may be incontinent and have no or minimal bladder control and as a result are unable to control when urination occurs. As a result of surgery, patients may have a partial bladder or colon, or it may be completely absent. Alternatively, other such people may be unable to manoeuvre themselves to a suitable convenience and therefore must rely on suitable means to remove waste material from the body in the position they are for the extended period, e.g. a bed or wheelchair.

The term 'ostomy patient' is used to describe a person who has undergone an ostomy operation. The term 'colostomy patient' and 'urostomy patient' are used mutatis mutandis.

Incapacitated people often use urine draining devices, e.g. urinary catheters, to aid in the removal of urine from the body. A urinary catheter is any tube system placed in the body to drain and collect urine from the bladder or the urethra. Urinary catheters are often used as a means to manage urinary incontinence in both men and women. There are a variety of different catheters including Foley, straight and coude-tip catheters, which are available in different forms and materials. For example, Foley catheters comprise a flexible plastic or rubber tube which is inserted into the bladder via the urethra to drain the urine. Such catheters include short term and long term catheters. Longer term catheters are often known as "indwelling catheters" and typically comprise a flexible tube connected to a drainage bag which collects the urine. Other indwelling catheters include supra-pubic catheters which are placed directly into the bladder through the abdomen at an insertion site located above the pubic bone. Such a catheter is typically inserted by an urologist during an outpatient surgery or office procedure. There have been developments in systems which are able to collect and drain urine from the body without the need for an intrusive catheter. Although such systems are not yet widely used, they do have advantages in terms of infection control and improved comfort and thus are likely to increase in usage.

With regard ostomy patients, there are many forms of ostomies. However, in general, ostomy patients have a portion of their intestinal or urinary system removed or diverted to a stoma. A stoma is an opening, created by the surgeon, where the intestinal or urinary system exits the patient at the body surface, generally terminating in a suitable collection reservoir such as a drainage bag, in a similar manner to catheter users.

Suitable drainage bags for catheter users and ostomy patients generally include pouches or so-called "leg bags" worn during the day, which provide a degree of mobility for the patient. Such pouches are used to collect waste material exiting the body. For catheter users, such waste material is generally urine and for ostomy patients it is either in the form of a stool or urine exiting the body via the stoma.

There is a plethora of different pouch systems for connection to a stoma, but in general all systems comprise a skin barrier (faceplate) which attaches to the body surface and provides a seal around the stoma, and a reservoir of some form. Some pouches are one-piece (i.e. the faceplate and reservoir are integral) and others are two-piece (i.e. the faceplate and reservoir are separable). The type of pouch used by a wearer depends on many variables which will not be discussed here.

At night, or during extended periods of immobility, e.g. bed-bound hours, it is necessary for catheter users and ostomy patients to connect to a reservoir of larger volume, typically referred to as a 'night bag'.

The night bag is usually hung on, placed next to or under a bed during the night and connected to the catheter user or ostomy patient via a flexible plastic or rubber tube. Typically, a catheter user or urostomy patient will pass around 1000 ml of urine into the night bag per night.

Typically, a catheter is connected to the night bag via a flexible tube.

An ostomy patient may connect to the night bag in various ways. In some cases, the night bag may connect, via the flexible tube, to an outlet provided on the pouch, i.e. the pouch effectively drains into the night bag. The night bag may alternatively attach to a faceplate already in place over the stoma; this is particularly suited to a two-piece system. Alternatively, in a slight variation, the flexible tube of the night bag can be provided with a faceplate to allow connection to the ostomy patient.

Night bags are particularly commonly used by urostomy patients, but may also be used by other ostomy patients as suitable and required.

Catheter users and ostomy patients are required to empty the contents of the night drainage bag each and every morning. It is typical to empty the contents of the bag into a sewer system of a dwelling, e.g. via a toilet. After emptying, the bag requires flushing and washing before being stored prior to reuse the following night.

The process of emptying and washing the night bag can be somewhat disheartening and often degrading to the user or patient, as well as being inconvenient and time consuming.

In addition, a night drainage bag is generally discarded after around a week of use and replaced by a new night drainage bag, resulting in significant expense to the user or health authority.

An improved night drainage apparatus for incapacitated people and ostomy patients is therefore required. Such apparatus might provide one or more of the following advantages:
discrete and less degrading to use;
reusable;
simple to use;
quick and easy to connect/disconnect;
easy to clean; and
inexpensive.

According to one aspect of the present invention, a drainage apparatus for an incapacitated person or ostomy patient having a urine draining device or stoma, the apparatus comprising a conduit having a first end having connection means suitable to attach to the urine draining device or stoma of the person or patient and a second end connected to a sewer/drainage system of a dwelling.

The term 'dwelling' will be understood to include all structures or vehicles suitable for living and, in particular, sleeping in. Such structures may, for example, include buildings, both commercial and domestic, caravans and motor homes, or similar.

The connection means may, in one embodiment, comprise means to attach to an outlet of a catheter. In another embodiment, the connection means may comprise means to attach to the outlet of an ostomy pouch, in particular, but not exclusively to, a urostomy pouch. Such connection means are known in the art. In another embodiment, the connection means may comprise means to attach to a faceplate; again, such means are known in the art, and are currently used to attach ostomy pouches to faceplates in two-piece systems. In another embodiment, the connection means may comprise a face plate to allow connection to the body surface of a patient around a stoma. Other connection means will be apparent to the person skilled in the art.

The conduit provides a flow path from the person or patient to the sewer/drainage system of the dwelling and will typically at least partially comprise flexible tubing.

In a preferred embodiment of the present invention, the conduit is permanently installed in the dwelling. However, in an alternative embodiment, a portion of the conduit comprising the connection means may be removable. This may be advantageous when the person or patient is sleeping away from home, e.g. in a hotel. Where this is the case, the second end of the conduit may be connected to sewer/drainage system or may be disposed directly into a bathroom convenience, suitably a toilet, into which the contents of the pouch, for example, is free to flow during the night.

The apparatus may suitably comprise a non-return valve. This prevents waste, particularly urine, from returning to the person or patient if, for example, there is a change in pressure in the drainage system. The non-return valve can be positioned at essentially any point in the apparatus. Preferably, a non-return valve is positioned at or near the point where the conduit is connected to the sewer/drainage system of the dwelling. More than one non-return valve may be provided as required.

In one embodiment, the conduit attaches to the sewer/drainage system of the dwelling via an adaptor. The adaptor serves to allow the conduit to attach to the sewer/drainage system of the dwelling, e.g. by allowing connection of the conduit to a plumbing pipe within the dwelling.

The plumbing pipe may be conventional and the precise requirements will depend on the particular circumstances. Typically, the plumbing pipe would comprise a branch off a soil pipe running to the adaptor, the branch running at a suitable angle to permit waste to flow to the soil pipe as required.

In an alternative embodiment, the conduit may comprise two parts, the first part comprising the connection means and extending to a wall of a dwelling. The second part extends from the wall to pre-existing sewer/drainage pipes within the dwelling. The first and second parts may suitably be separable, and may be connected via an adaptor. Thus, in this embodiment, it can be seen that the conduit extends beyond the room where the person or patient is located, and extends to a pre-existing sewer/drainage system in the dwelling. Suitably, the first part of the conduit is a flexible tube, and the second part a comparatively rigid tube.

The branch or second part of the conduit may be connected to the soil pipe of a dwelling via a standard 'boss' fitting, however other suitable connecting means may be used.

The adaptor may conveniently comprise a non-return valve.

Preferably, the adaptor is mounted on a wall in a room. Advantageously, it may be provided in a socket, and the socket may be similar in appearance to a standard electric or telephone socket which may help the adaptor to blend in with other wall-mounted sockets located within the dwelling. The adaptor should in general be positioned such that it is lower than the catheter or stoma, such that waste runs effectively from the person or patient, e.g. while in bed.

Preferably, the adaptor is located in a bedroom of the dwelling and near the bed in which the person or patient sleeps. It may be convenient to provide a plurality of adaptors; one or more being located in more than one room in the dwelling, e.g. near an armchair or sofa in the living room in which the person or patient may sit for an extended period.

Pumping means may be incorporated in the apparatus in circumstances where a general negative gradient is not achievable and/or the apparatus does not drain sufficiently under the influence of gravity.

Importantly, the non-return valve provided in the adaptor prevents air and smells entering the room when the conduit is not connected to the person or patient, or the conduit has been disconnected from the adaptor. Advantageously, the valve may be replaceable. Suitable valves are well known in the art.

Preferably the conduit extending from the person or patient is flexible and resistant to collapse. Resistance to collapse may be achieved by providing reinforcing rings or a helix around the conduit.

Preferably, the conduit is formed of plastics material and suitable to withstand staining and corrosion, particularly by urine.

According to a second aspect of the invention, there is provided a drainage system comprising:
 a conduit having a first end having connecting means suitable to attach to a urine draining device or stoma of an incapacitated person or ostomy patient and a second end adapted to connect to a sewer/drainage system of a dwelling.

Suitably, the system may comprise one or more of:
 at least one adaptor suitable for connecting the conduit to a sewer/drainage system, preferably comprising a one-way valve;
 one or more brackets to secure a portion of the conduit to a wall of a dwelling;
 a joint, e.g. a 'boss' joint, to connect an end of a conduit to a sewer/drainage pipe;
 a syringe, suitably adapted for flushing the conduit; and
 a plug for sealing a free end of the conduit when not connected to the urine draining device or stoma.

A dwelling comprising such an apparatus or system as described above is also provided.

Figure 2:
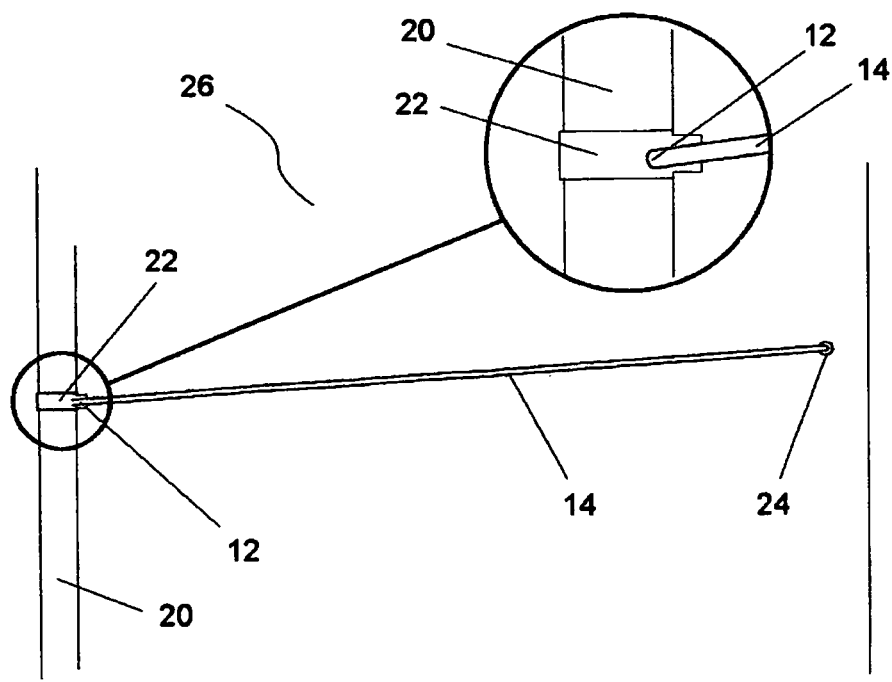
Figure 3:
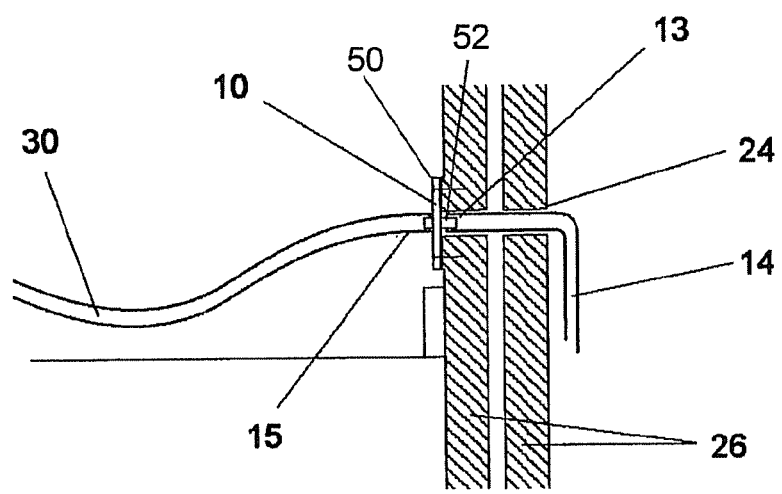
Figure 4:
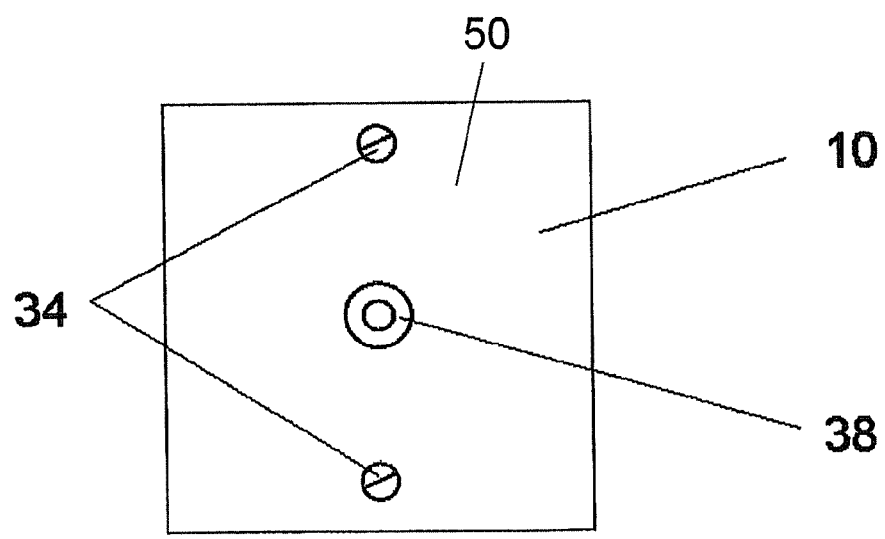
Figure 5:
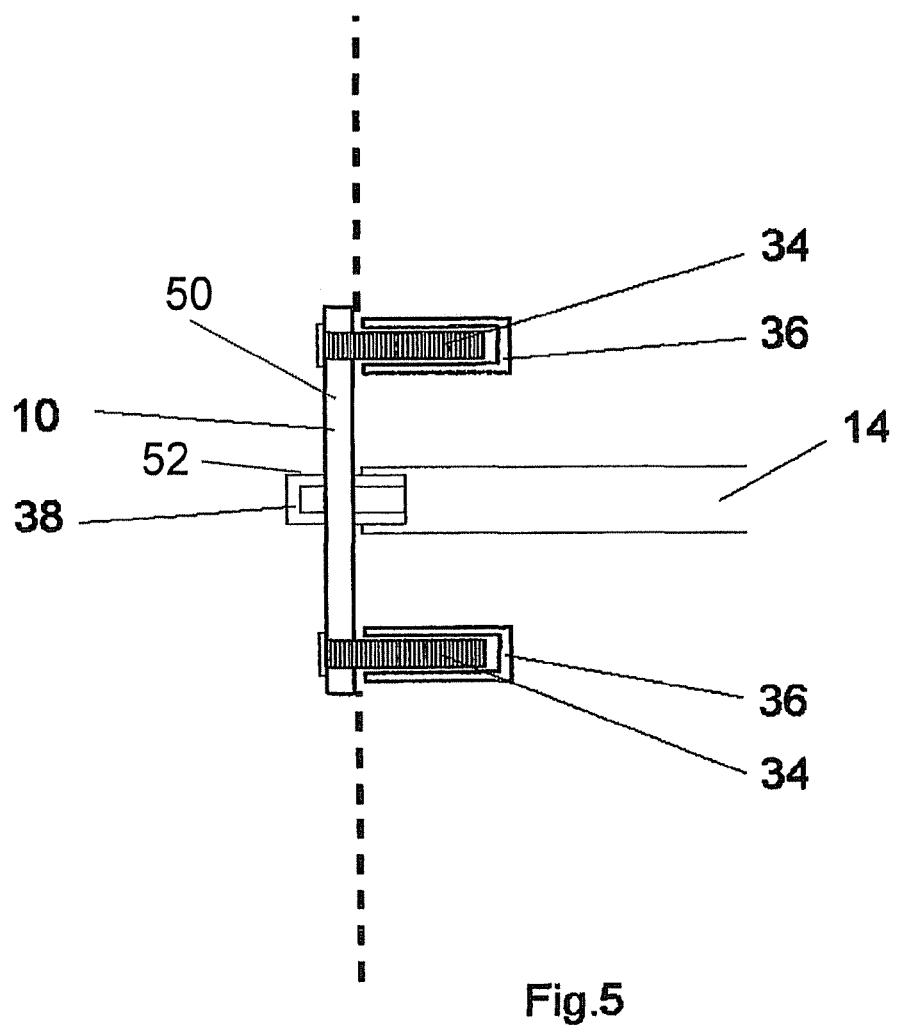

An embodiment of the present invention will now be described, by way of example only, with reference to the accompanying drawings, in which:
 FIG. 1 is a cross section through a dwelling in which apparatus according to the present invention is installed;
 FIG. 2 is a schematic showing connection of the apparatus to a soil pipe;
 FIG. 3 is a schematic showing a section through the adaptor (socket);
 FIG. 4 is a schematic front view of one embodiment of the adaptor (socket); and
 FIG. 5 is a cross-sectional view showing the adaptor (socket) of FIG. 4 mounted in a wall.

An apparatus for incapacitated people or ostomy patients, especially urine draining device users or urostomy and colostomy patients who wear a pouch, comprises a conduit (30) having a first end having connection means to attach to a urine draining device or stoma of the person or patient and a second end adapted to connect to a sewer/drainage system of a dwelling (8). The conduit (30) provides a flow path from the conduit or stoma to the sewer/drainage system of the dwelling (8), particularly during sleeping hours when the person or patient is in bed (18) or when the person or patient is immobile for extended periods, e.g. in hospital. As described above, the connection means may provide connection of the first end of the conduit (30) to a catheter of the incapacitated person, for example. Alternatively, the connection means may provide connection of the first end of the conduit (30) to the stoma of the patient via a faceplate or via a pouch.

The conduit (30) fluidly connects the catheter, stoma or pouch outlet (not shown) to a soil pipe (20) of an existing sewer/drainage system of the dwelling (8) via an adaptor (socket) (10) and a plumbing pipe (14).

The socket (10) is located, for example, in a bedroom (16) of the dwelling (8), preferably near the bed (18) of the person or patient and below the position of the catheter or stoma when the person or patient is in bed. This allows for waste from the person or patient to flow towards the socket (10) under the influence of gravity via the conduit (30).

With reference to FIG. 2, a portion of the plumbing pipe (14) extends through a hole (24) in an external wall (26) of the dwelling (8), in the vicinity of the socket (10), and runs along the outside wall of the dwelling (8). The plumbing pipe (14) is secured to the outside of the dwelling (8) by suitable means, e.g. brackets (not shown). The plumbing pipe (14) may be similar in appearance to existing exterior drainage infrastructure, e.g. the soil pipe or downpipes leading from roof guttering. The plumbing pipe (14) is arranged to allow the waste to flow downhill from the socket (10) to the soil pipe (20) under the force of gravity. An end (12) of the plumbing pipe (14) is connected to the soil pipe (20), running vertically down the outside of the dwelling (8), by a standard boss fitting (22) mounted in the side of the soil pipe (20). However, other suitable connecting means may be used.

With reference to FIG. 3, the plumbing pipe (14) passes through the hole (24) in the external wall (26) of the dwelling (8) and is connected at an end (13) to the socket (10). The socket (10) is wall-mounted in the bedroom of the dwelling. Whilst the person or patient is in bed, the catheter, stoma or pouch outlet (not shown) is located higher than the socket (10) and is connected to the socket (10) by the conduit (30). The socket (10) is adapted to receive an end (15) of the conduit (30) providing quick and easy connection and disconnection with the socket (10). Socket (10) comprises a plate (50) for fixedly attaching to wall (26) and a member (52) having a first end for conduit (30) to detachably connect and a second end for coupling with plumbing pipe (14).

With reference to FIGS. 4 and 5, the socket (10) is similar in appearance to a standard electric or telephone socket helping it blend in with the interior of the dwelling (8). The socket (10) is mounted to the wall (26) of a room by screws (34) and wall plugs (36). The member of the socket (10) includes a one-way valve (38) and is disposed centrally in the socket (10) which allows waste to flow through the valve (38) and into the second tube (14) but prevents waste (liquid or gas) passing back through the valve (38). This is particularly important to prevent waste and/or smells entering the room when either the catheter or stoma is not connected to the conduit (30) or when the conduit (30) is not connected to the socket (10), e.g. when the apparatus is not in use. The valve (38) is suitably adapted to receive the end (15) of the conduit (30).

When the person or patient retires to bed (18), he simply connects an end (not shown) of the conduit (30) to the outlet of the catheter or urostomy pouch or direct to the stoma via a faceplate and, if required, plugs the other end (15) of the conduit (30) into the socket (10). The conduit (30) may be left in the socket (10) when not in use and only the catheter, faceplate or pouch outlet need connecting to the conduit (30). As bodily waste, e.g. urine, leaves the patient via the catheter or stoma during the night, it flows under the influence of gravity from the catheter or stoma to the adaptor (10) via the conduit (30). The waste then flows through the one-way valve (38) and enters the plumbing pipe (14) to flow, under the influence of gravity, into the soil pipe (20) of the sewer/drainage system.

When the person or patient awakes and leaves his bed (18), he simply disconnects the catheter, faceplate or the pouch outlet from the conduit (30). The conduit (30) may be left in the socket (10) or removed and stored until the apparatus is used again. Where the conduit (30) is left in the socket (10), a free end of the conduit (30) may be elevated above the socket (10) to allow any waste remaining in the conduit (30) to be drained through the valve (38) and into the plumbing pipe (14). If the conduit (30) contains a small volume of waste which will not drain away, a small plug or bung (not shown) may be included to contain this small amount of waste when the apparatus is not being used.

The apparatus can be flushed out periodically using suitable means. Such means could include a suitably adapted syringe which connects with the socket (10) or, alternatively, the free end of the conduit (30) when the catheter, faceplate or pouch outlet is not connected. The syringe may force water, or cleaning agent, through the apparatus.

The conduit (30) is substantially flexible and the plumbing pipe (14) is substantially rigid and both are resistant to collapse. Both the conduit (30) and plumbing pipe (14) are formed of plastics material and preferably resistant to corrosion and staining by urine.

What is claimed is:

1. A drainage system for a dwelling to aid an incapacitated person or ostomy patient having a urine draining device or stoma respectively, the system comprising first and second separable conduit parts connectable at first ends by an adaptor, wherein the first conduit part is substantially flexible and comprises attachment means for detachably connecting a second end thereof to the urine draining device or stoma of the person or patient;

the second conduit part is comparatively rigid and adapted to extend from the adaptor and connect at a second end to an external sewer/drainage pipe of the dwelling and be permanently installed therein;

the adaptor comprising a plate configured to fixedly attach to a wall of the dwelling below the urine draining device or stoma when in use, the adaptor further comprising a member having a first end for the first conduit part to detachably connect and a second end configured to couple to the second conduit part; the member further comprising a non-return valve to allow urine to flow through the valve and into the second conduit part whilst preventing the same passing back through the valve and into the first conduit part;

wherein the first end is tubular and inserted within the first conduit so that the first conduit surrounds the first end, and the second end is tubular and inserted within the second conduit so that the second conduit surrounds the second end.

2. The drainage system according to claim 1, wherein the attachment means is adapted to attach to an outlet of a catheter or ostomy pouch or to a faceplate to allow connection to the body surface of the patient around the stoma.

3. The drainage system according to claim 1, wherein the second conduit part is connected to a soil pipe of the dwelling via a standard 'boss' fitting.

4. The drainage system according to claim 1, wherein the first and second conduit parts are formed of plastics material and resistant to staining and corrosion, particularly by urine.

5. The drainage system according to claim 1, wherein the system comprises one or more of the following:
- one or more brackets to secure a portion of the second conduit part to a wall of a dwelling;
- a syringe for flushing the system ; and
- a plug for sealing a free end of the first conduit part when not connected to the urine draining device or stoma or adaptor.

6. A dwelling comprising the drainage system according to claim 1.

\* \* \* \* \*